(12) United States Patent
Hybertson et al.

(10) Patent No.: US 11,786,483 B2
(45) Date of Patent: Oct. 17, 2023

(54) COMPOSITIONS AND METHODS FOR TREATMENT OR PREVENTION OF ORAL MUCOSITIS

(71) Applicant: PATHWAYS BIOSCIENCE, LLC, Aurora, CO (US)

(72) Inventors: Brooks Michael Hybertson, Boulder, CO (US); Joe Milton McCord, West Palm Beach, FL (US)

(73) Assignee: PATHWAYS BIOSCIENCE, LLC, Aurora, CO (US)

( * ) Notice: Subject to any disclaimer, the term of this patent is extended or adjusted under 35 U.S.C. 154(b) by 610 days.

(21) Appl. No.: 16/813,650

(22) Filed: Mar. 9, 2020

(65) Prior Publication Data
US 2020/0206156 A1 Jul. 2, 2020

Related U.S. Application Data

(63) Continuation-in-part of application No. 15/757,281, filed as application No. PCT/US2016/050263 on Sep. 2, 2016, now abandoned.

(60) Provisional application No. 62/213,539, filed on Sep. 2, 2015.

(51) Int. Cl.
| | |
|---|---|
| *A61K 31/12* | (2006.01) |
| *A61K 47/46* | (2006.01) |
| *A61K 47/40* | (2006.01) |
| *A61K 9/00* | (2006.01) |

(52) U.S. Cl.
CPC .............. *A61K 31/12* (2013.01); *A61K 47/40* (2013.01); *A61K 47/46* (2013.01); *A61K 9/006* (2013.01); *A61K 9/0014* (2013.01)

(58) Field of Classification Search
CPC ........ A61K 31/12; A61K 47/40; A61K 47/46; A61K 9/0014; A61K 9/006
USPC ........................................................ 514/125
See application file for complete search history.

(56) References Cited

U.S. PATENT DOCUMENTS

| | | |
|---|---|---|
| 2007/0021357 A1 | 1/2007 | Tobla et al. |
| 2007/0238755 A1 | 10/2007 | Hauer-Jensen et al. |
| 2011/0245316 A1 | 10/2011 | Rios |
| 2015/0005266 A1 | 1/2015 | Purcell |

FOREIGN PATENT DOCUMENTS

EP 875240 A2 4/1998

OTHER PUBLICATIONS

Cho et al. (2010) "Nrf2 protects against airway disorders." Toxicol Appl Pharmacol, 244(1), pp. 43-56.
Eggler et al. (2008) "Molecular mechanisms of natural products in chemoprevention: induction of cytoprotective enzymes by Nrf2." Mol Nutr Food Res, 52 Suppl 1, pp. S84-S94.
Elad et al. (2013) "Topical curcumin for the prevention of oral mucositis in pediatric patients: case series." Altern Ther Health Med, 19(3), pp. 21-24.
Francis et al. (2014) Abstract of "Effectiveness of Indian Turmeric Powder with Honey as Complementary Therapy on Oral Mucositis : A Nursing Perspective among Cancer Patients in Mysore." Nurs J India, 105(6), pp. 258-260.
Gao et al. (2014) "The clinical potential of influencing Nrf2 signaling in degenerative and immunological disorders." Clin Pharmacol, 6, pp. 19-34.
Huang et al. (2015) "The complexity of the Nrf2 pathway: Beyond the antioxidant response." The Journal of Nutritional Biochemistry, 26, pp. 1401-1413.
Koehn et al. (2005) "The evolving role of natural products in drug discovery." Nat Rev Drug Discov 4(3): 206-220.
Lee (2010) "Discovery and development of natural product-derived chemotherapeutic agents based on a medicinal chemistry approach." J Nat Prod, 73(3), pp. 500-516.
Luer et al. (2011) "Topical curcumin can inhibit deleterious effects of upper respiratory tract bacteria on human oropharyngeal cells in vitro: potential role for patients with cancer therapy induced mucositis?" Support Care Cancer, 19(6), pp. 799-806.
Luer et al. (2014) "Synthetic versus natural curcumin: bioequivalence in an in vitro oral mucositis model." BMC Complement Altern Med, 14, p. 53.
Maher et al. (2010) "The rise of antioxidant signaling—the evolution and hormetic actions of Nrf2." Toxicol Appl Pharmacol, 244(1), pp. 4-15.
Niture et al. (2014) "Regulation of Nrf2—an update." Free Radical Biology and Medicine, 66, pp. 36-44.
Reisman et al. (2015) "Topical application of RTA 408 lotion activates Nrf2 in human skin and is well-tolerated by healthy human volunteers." BMC Dermatol, 15(1), p. 10.
Reisman et al. (2014) "Topical application of the synthetic triterpenoid RTA 408 protects mice from radiation-induced dermatitis." Radiat Res, 181(5), pp. 512-520.
Reisman et al. (2014) "Topical application of the synthetic triterpenoid RTA 408 activates Nrf2 and induces cytoprotective genes in rat skin." Arch Dermatol Res, 306(5), pp. 447-454.
Rezvani et al. (2004) "Modification of radiation-induced acute oral mucositis in the rat." Int J Radiat Biol, 80(2), pp. 177-182.
Satoh et al. (2010) "Nrf2-deficiency creates a responsive microenvironment for metastasis to the lung." Carcinogenesis, 31(10), pp. 1833-1843.
Shukla et al. (2012) "Profiling environmental chemicals for activity in the antioxidant response element signaling pathway using a high throughput screening approach." Environ Health Perspect, 120(8), pp. 1150-1156.
Simmons (2011) "NRF2 Oxidative Stress Induced by Heavy Metals is Cell Type Dependent." Curr Chem Genomics, 5, pp. 1-12.
Sonis (2011) "Oral mucositis." Anticancer Drugs, 22(7), pp. 607-612.
Villa et al. (2015) "Mucositis: pathobiology and management." Curr Opin Oncol, 27(3), pp. 159-164.
Yuan et al. (2014) "Emerging therapies for the prevention and treatment of oral mucositis." Expert Opin Emerg Drugs, 19(3), pp. 343-351.

(Continued)

*Primary Examiner* — Kristin A Vajda
(74) *Attorney, Agent, or Firm* — COZEN O'CONNOR

(57) ABSTRACT

Radiation therapy or chemotherapy may cause oral mucositis. Compositions and methods are disclosed here which prevent and/or treat oral mucositis caused by radiation therapy or chemotherapy. The compositions are also effective in treating a number of skin disorders.

18 Claims, 7 Drawing Sheets

(56) References Cited

OTHER PUBLICATIONS

Sung et al. "Cancer Cell Signaling Pathways Targeted by Spice-Derived Nutraceuticals," NIH 1-3, 7-21, 24-25—Public Access, May 6, 2013 (May 6, 2013), pp. 1-43.

International Search Report and Written Opinion of PCT/US2016/050263 dated Dec. 7, 2016, 12 pp.

Nathir, A.F. et al., Physicochemical study on microencapsulation of hydroxypropyl-β-cyclodextrin in dermal preparations, Drug Development and Industrial Pharmacy,vol. 36, 2010—Issue 6, pp. 688-697 (Year: 2010).

Oliver et al (EP 875240 translation) (Year: 1998).

Ji et al zuoInclusion Complex of Dibenzoylmethane with βcyclodextrin (Advanced Materials Research, (2011) vols. 239-242, pp. 1879-1882).

Lieder et al "Identification of UV-protective activators of nuclear factor erythroid derived 2-related factor 2 (Nrf2) by combining a chemical library screen with computer-based virtual screening" (20120 Institute of Molecular Health Sciences, Department of Biology, ETH Zurich, 26 pages, 2012.

Damiani et al "Nitroxide radicals protect dna from damage when illuminated in vitro in the presence of dibenzoylmethane and a common sunscreen ingredient"; Free Radical Biology & Medicine, vol. 26. Nos. 7/8, pp. 809-816, 1999.

U.S. Appl. No. 15/757,281 Office Action dated Dec. 10, 2019, 13 pages.

U.S. Appl. No. 15/757,281 Office Action dated Jun. 12, 2019, 10 pages.

U.S. Appl. No. 15/757,281 Office Action dated Nov. 29, 2018, 10 pages.

COMPOSITIONS AND METHODS FOR TREATMENT OR PREVENTION OF ORAL MUCOSITIS

RELATED APPLICATIONS

This application is a Continuation-in-Part of U.S. patent application Ser. No. 15/757,281 filed Mar. 2, 2018, which claims priority to U.S. Patent application 62/213,539 filed Sep. 2, 2015, the entire contents of the above-mentioned applications are hereby incorporated by reference into this application.

BACKGROUND

I. Field of the Invention

The present invention relates generally to the chemical compound: 1,3-diphenyl-1,3-propanedione (CAS number [120-46-7], also referred to herein as dibenzoylmethane, DBM or PB201). The present invention also relates to its chemical derivatives, methods of their use, pharmaceutical compositions thereof, and kits and articles of manufacture thereof.

II. Description of the Related Art

Oral mucositis is a common and harmful side effect of radiation therapy and chemotherapy in cancer patients that can be dose-limiting, impairing the clinical ability to continue the otherwise needed therapy and that also greatly impacts the patient's quality of life due to pain, loss of function, and increased infections (Sonis, Oral mucositis, Anticancer Drugs 22, 607-612 (2011); Yuan and Sonis, Emerging therapies for the prevention and treatment of oral mucositis, Expert Opin Emerg Drugs 19, 343-351 (2014); Villa and Sonis, Mucositis: pathobiology and management, Curr Opin Oncol 27, 159-164 (2015)). It affects nearly 500,000 patients in the US annually. Oral mucositis occurs at a relatively high frequency in both radiation and chemotherapy patients, and has a significant negative impact on the clinical ability to apply effective dosage to patients.

SUMMARY

The presently disclosed instrumentalities advance the art by providing compositions that help treat or prevent diseases such as oral mucositis. In one embodiment, the disclosed compositions induce gene expression by the Nrf2-dependent pathway. In another embodiment, by activating the Nrf2-dependent pathway, the disclosed compositions help protect the epidermal and dermal cells prior to radiation therapy or chemotherapy. In another embodiment, the disclosed compositions help treat or repair affected skin cells shortly after the radiation or chemotherapy.

1,3-diphenyl-1,3-propanedione (also known as dibenzoylmethane (DBM), and also referred to here as PB201) and some of its chemical derivatives are candidates for drug development (Koehn and Carter, The evolving role of natural products in drug discovery, Nat Rev Drug Discov 4, 206-220 (2005); Lee, Discovery and development of natural product-derived chemotherapeutic agents based on a medicinal chemistry approach, J Nat Prod 73, 500-516 (2010)).

One aspect of the present disclosure is the use of 1,3-diphenyl-1,3-propanedione and its derivatives (or analogs) to induce gene expression by the Nrf2-dependent pathway.

In one embodiment, it is shown here that 1,3-diphenyl-1,3-propanedione (PB201) induces Nrf2 activation and subsequent gene expression of an ARE-driven reporter gene in mammalian cells, specifically human cancer cell lines from liver, breast, brain, kidney, and lung tissues. In another embodiment, the combination of 1,3-diphenyl-1,3-propanedione with other agents and other Nrf2 activators causes a synergistic increase in activation.

In one embodiment, the composition may contain dissolution or suspension of 1,3-diphenyl-1,3-propanedione into liquid, gel, lotion, or ointment formulations.

In another embodiment, the composition may contain dissolution or suspension of structurally-related analogs of 1,3-diphenyl-1,3-propanedione, including but not limited to 1,3-Dibenzoylpropane, 2-Bromo-1,3-diphenylpropane-1,3-dione, 2-Fluoro-1,3-diphenylpropane-1,3-dione, Benzoic anhydride, 1,3-Bis(4-methoxyphenyl)-1,3-propanedione, 1-(2-Hydroxyphenyl)-3-phenyl-1,3-propanedione, 2-Fluoro-1,3-bis(perfluorophenyl)propane-1,3-dione, 1,3-Bis(2-fluorophenyl) propane-1,3-dione, or 2-Fluoro-1,3-bis(4-fluorophenyl)propane-1,3-dione into liquid, gel, lotion, or ointment formulations that effect Nrf2 activation in cells.

In another embodiment, the composition may contain 1,3-diphenyl-1,3-propanedione (DBM) formulated into an aqueous solution or suspension by the addition of 2-hydroxypropyl beta-cyclodextrin (HPBCD). In another embodiment, the molar ratio between DBM and HPBCD may be between 1:1 to 1:5, or about 1:3.

In another embodiment, the solution or suspension of 1,3-diphenyl-1,3-propanedione may be used by topical treatment within the oral cavity for the prevention or treatment of oral mucositis. It may be used as a liquid, gel, lotion, or ointment to effect Nrf2 activation, expression of cellular protection genes in the mucosal cells, as well as therapeutic benefit against oral mucositis.

In another embodiment, the 1,3-diphenyl-1,3-propanedione may be in a local or topical administration, for example, by applying to the skin or epithelial surface of the oral cavity in the form of liquid suspension, lotion, gel, ointment, mouthwash, or aqueous spray.

In another embodiment, the local or topical administration of 1,3-diphenyl-1,3-propanedione or analogs thereof may be for the treatment of skin conditions including, for example, irritation, rashes, infections, burns, insect bites, and sunburn.

In one aspect, the dosage of DBM when applied to human may be between 1 μg and 1000 μg applied at least once daily. For example, the frequency may be 1×, 2×, 3× or more per day. In another aspect, the dosage of DBM may be between 10 μg and 1000 μg at least once daily, or between 50 μg and 500 μg at least once daily. In another aspect, the disclosed composition may be applied topically at least once daily, wherein the composition comprises an aqueous DBM solution, and the concentration of DBM is between 5 and 50 μg/mL (22 to 223 μM), and the volume of the composition is sufficient to cover the oral mucositis surface.

In another embodiment, the 1,3-diphenyl-1,3-propanedione may be formulated into an aqueous solution or suspension for local or topical administration by mixing with a complexing agent. Examples of complexing agent may include but are not limited to the HPBCD mentioned above, or agents that facilitate the formation of liposomal formulations of 1,3-diphenyl-1,3-propanedione, such as dimyristoylphosphatidylcholine (DMPC), dipalmitoylphosphatidylcholine (DPPC), and dimyristoylphosphatidylglycerol (DMPG).

In another embodiment, compositions containing the 1,3-diphenyl-1,3-propanedione or combination thereof may be administered as a component within a bandage or pad applied to the skin or to a wound.

In another embodiment, compositions containing the 1,3-diphenyl-1,3-propanedione or combination thereof may be administered orally, for example in the form of a tablet, capsule, syrup, aqueous infusion, alcohol-extract, or powder.

In another embodiment, compositions containing the 1,3-diphenyl-1,3-propanedione or combination thereof may be administered in the form of an aerosol. For example, by administration to the lungs in the form of a fine aerosol mist or powder which is inhaled and partially deposited within the lung airways.

DETAILED DESCRIPTION

Figure 1:
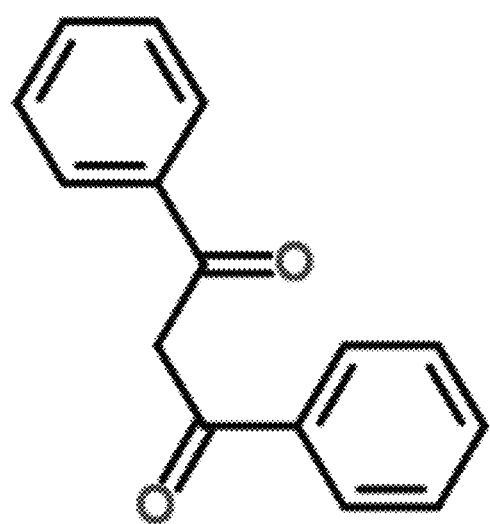
FIG. 1 shows the structure of 1,3-diphenyl-1,3-propanedione.

The present disclosure relates to the chemical compound: 1,3-diphenyl-1,3-propanedione CAS number [120-46-7], and chemical derivatives thereof, methods of use thereof.

The present disclosure pertains to the use of 1,3-diphenyl-1,3-propanedione as a therapeutic agent that activates the Nrf2 (NFE2L2, Nuclear Factor Erythroid 2-Like 2) cell signaling pathway, upregulates radioprotective, antioxidant, and anti-inflammatory genes, and therefore facilitates prevention and/or treatment of oral mucositis.

Nuclear factor-erythroid 2 related factor 2 (Nrf2) is a transcription factor that is kept in check by Kelch-like ECH-Associated Protein 1 (Keap1) and that regulates the gene expression of a wide variety of cytoprotective phase II detoxification enzymes and antioxidant enzymes through an enhancer sequence known as the antioxidant-responsive element (ARE) (Maher and Yamamoto, The rise of antioxidant signaling—the evolution and hormetic actions of Nrf2, Toxicol Appl Pharmacol 244, 4-15 (2010); Satoh, Moriguchi, Taguchi, Takai, Maher, Suzuki, Winnard, Raman, Ebina, Nukiwa and Yamamoto, Nrf2-deficiency creates a responsive microenvironment for metastasis to the lung, Carcinogenesis 31, 1833-1843 (2010)).

The ARE is a promoter element found in many antioxidant enzymes, including superoxide dismutase (SOD), peroxiredoxins, thioredoxins, catalase, glutathione peroxidase, and heme oxygenase-1 (HO-1). Nrf2 plays a pivotal role in the ARE-driven cellular defense system against oxidative stress (Niture, Khatri and Jaiswal, Regulation of Nrf2-an update, Free Radical Biology and Medicine 66, 36-44 (2014); Huang, Li, Su and Kong, The complexity of the Nrf2 pathway: Beyond the antioxidant response, The Journal of Nutritional Biochemistry in press (2015)). This has made agents that act on the Nrf2/Keap1/ARE pathway of great scientific interest for their possible use as therapeutic agents (Gao, Doan and Hybertson, The clinical potential of influencing Nrf2 signaling in degenerative and immunological disorders, Clin Pharmacol 6, 19-34 (2014); Niture, Khatri and Jaiswal, Regulation of Nrf2-an update, Free Radical Biology and Medicine 66, 36-44 (2014)).

One specific aspect of the present disclosure includes a method of use of a topical formulation containing 1,3-diphenyl-1,3-propanedione to prevent and/or treat oral mucositis caused by radiation therapy or chemotherapy. Examples of such formulations include, but are not limited to, liquid solutions, suspensions, gels, lotions, ointments, mouthwashes, and sprays. In one embodiment, aloe extract may be utilized as a viscous liquid or gel carrier for the 1,3-diphenyl-1,3-propanedione active agent.

By way of example, a number of embodiments of the present disclosure are listed below:

1. A composition comprising an agent for the prevention or treatment of oral mucositis in a mammal, said agent activates the Nrf2 signaling pathway.

2. The composition of Item 1, wherein the agent is 1,3-diphenyl-1,3-propanedione (DBM) or a derivative (or analog) of DBM wherein the derivative of DBM is selected from the group consisting of 1,3-diphenyl-1,3-propanedione, 1,3-Dibenzoylpropane, 2-Bromo-1,3-diphenylpropane-1,3-dione, Benzoic anhydride, 1,3-Bis(4-methoxyphenyl)-1,3-propanedione, and 1-(2-Hydroxyphenyl)-3-phenyl-1,3-propanedione.

3. The composition of any of the preceding Items, further comprising 2-hydroxypropyl beta-cyclodextrin (HPBCD).

4. The composition of any of the preceding Items, wherein the molar ratio between DBM and HPBCD is between about 1:1 and 1:5

5. The composition of any of the preceding Items, wherein the molar ratio between DBM and HPBCD is about 1:3.

6. The composition of any of the preceding Items, further comprising water and one or more solubility enhancing agents from the group consisting of surfactants, liposomes, amphiphiles, emulsifiers, and complexing agents.

7. The composition of any of the preceding Items, wherein the composition is formulated for topical administration.

8. The composition of any of the preceding Items, wherein the composition is formulated for administration to the skin or to the oral cavity.

9. The composition of any of the preceding Items, wherein the composition is in the form selected from the group consisting of liquid, gel, cream, and lotion.

10. The composition of any of the preceding Items, wherein the composition is in the form of a nutritional supplement.

11. The composition of any of the preceding Items, further comprising one or more additional Nrf2-activating agents.

12. A method for preventing and/or treating oral mucositis in a mammal, comprising administering to the mammal a therapeutically effective amount of 1,3-diphenyl-1,3-propanedione (DBM).

13. The method of Item 12, wherein the mammal is a human.

14. The method of any of Items 12-13, wherein the administration is through topical application.

15. The method of any of Items 12-14, wherein the administration is applying the composition to the skin or oral cavity of a mammal.

16. The method of any of Items 12-15, wherein the administration is through oral application.

17. The method of any of Items 12-16, wherein the mammal has a disease or condition caused by oxidative stress, detoxification, inflammation, or cancer.

18. The method of any of Items 12-17, wherein the mammal has a disease or condition caused by radiation therapy or chemotherapy.

19. The method of any of Items 12-18, wherein the mammal has a radiation-induced oral mucositis or chemotherapy-induced oral mucositis.

20. The method of any of Items 12-19, wherein the mammal has a radiation-induced dermatitis.

21. The method of any of Items 12-20, wherein the composition further comprises 2-hydroxypropyl beta-cyclodextrin (HPBCD).

22. The method of any of Items 12-21, wherein the molar ratio between DBM and HPBCD is between about 1:1 and 1:5.

23. A pharmaceutical composition for treating oral mucositis, comprising the composition of Items 1-11 and a pharmacologically acceptable salt.

24. A method for the treatment of skin conditions including irritation, abrasions, rashes, infections, burns, insect bites, contact dermatitis, and sunburn in a mammal, comprising administering to the mammal a therapeutically effective amount of 1,3-diphenyl-1,3-propanedione (DBM).

It will be readily apparent to those skilled in the art that the compositions and methods described herein may be modified and substitutions may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLE 1

Properties of PB201

As an example of the properties of PB201, cell lines were cultured which had been stably transfected with constructs of the luciferase gene. This luciferase gene was driven in its promoter region by copies of the ARE Nrf2-binding sequence, known as promoter-reporter constructs (Simmons, Fan, Yeoman, Wakefield and Ramabhadran, NRF2 Oxidative Stress Induced by Heavy Metals is Cell Type Dependent, Curr Chem Genomics 5, 1-12 (2011); Shukla, Huang, Simmons, Tice, Witt, Vanleer, Ramabhadran, Austin and Xia, Profiling environmental chemicals for activity in the antioxidant response element signaling pathway using a high throughput screening approach, Environ Health Perspect 120, 1150-1156 (2012)).

Figure 2:
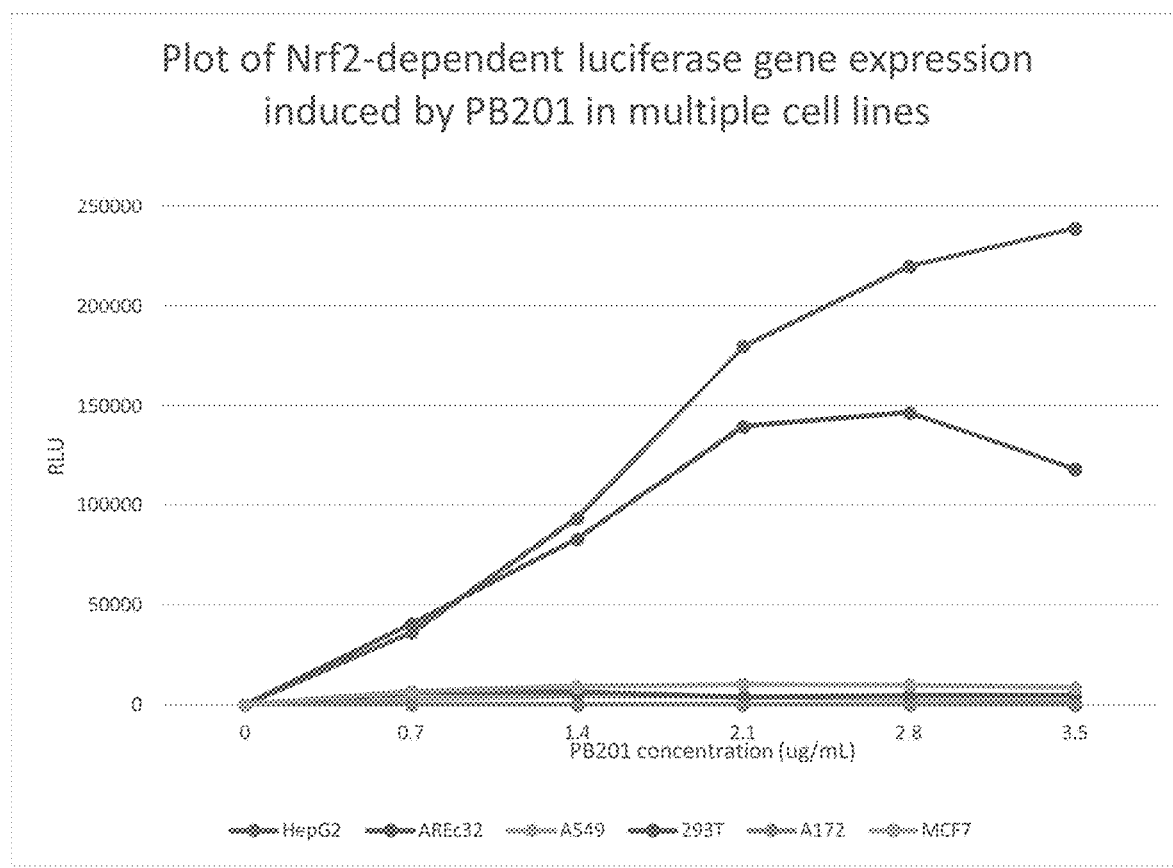
FIG. 2 shows overlay of relative light units (RLU) observed with added luciferin after ARE-driven luciferase gene expression was induced by treatment with PB201 in stably transfected HepG2 (human liver), AREc32 (human breast), MCF7 (human breast), A549 (human lung), 293T (human kidney), and A172 (human brain) cancer cell lines.
Figure 3:
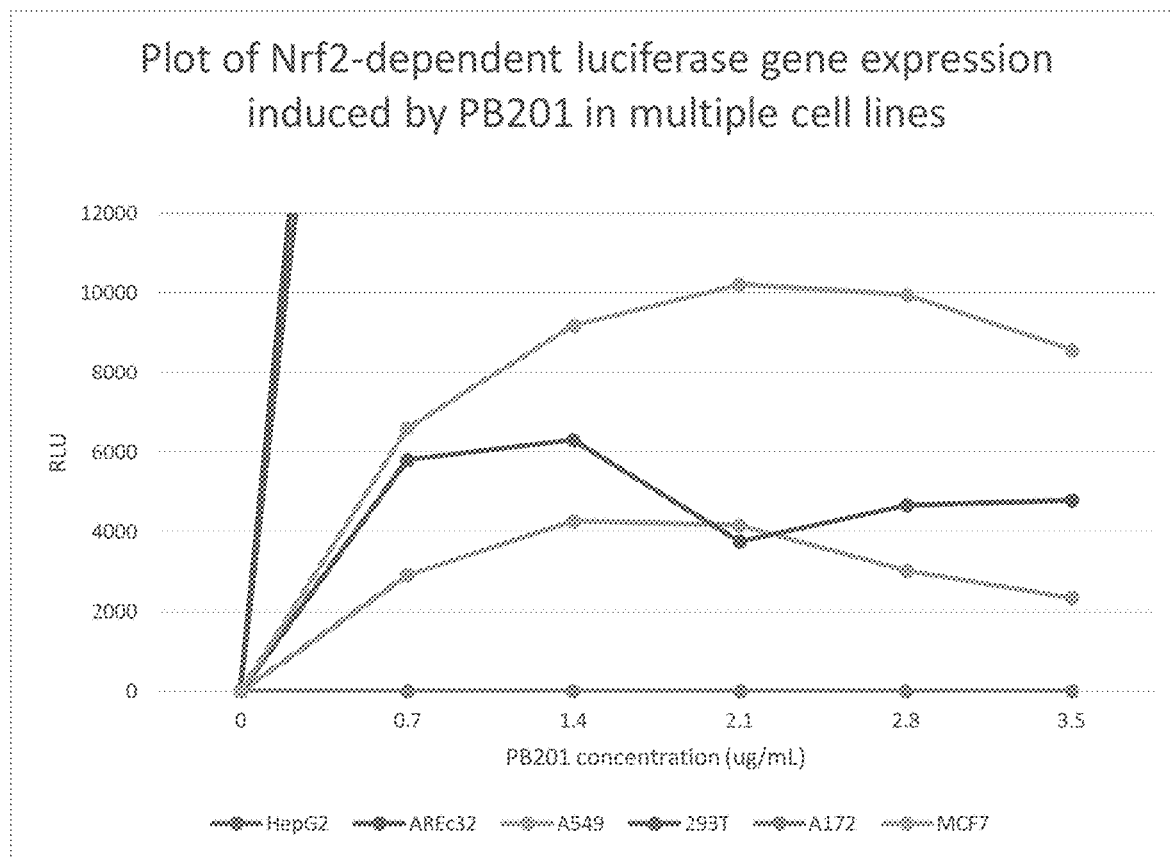
FIG. 3 shows zoom in on overlay of relative light units (RLU) observed with added luciferin after ARE-driven luciferase gene expression was induced by treatment with PB201 in stably transfected HepG2 (human liver), AREc32 (human breast), MCF7 (human breast), A549 (human lung), 293T (human kidney), and A172 (human brain) cancer cell lines.
Figure 4:
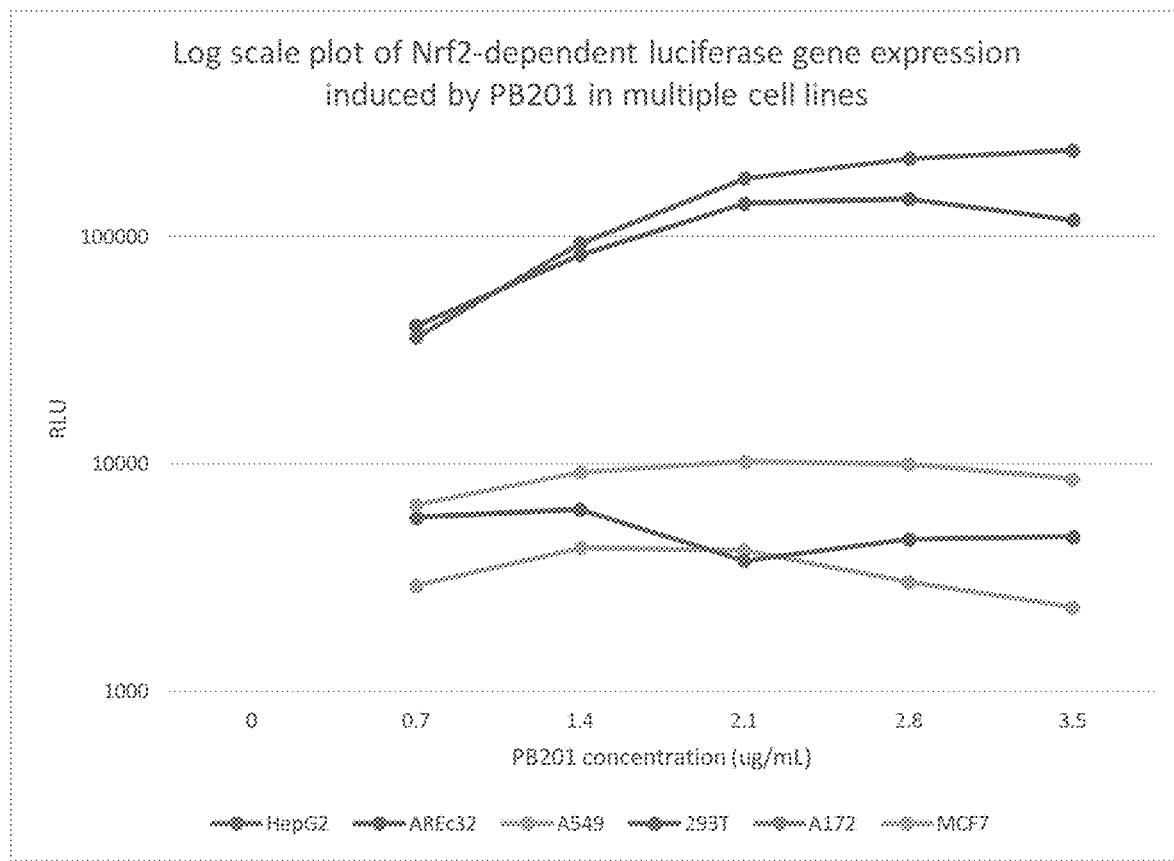
FIG. 4 shows a zoom in using log scale for the RLU y-axis on overlay of relative light units (RLU) observed with added luciferin after ARE-driven luciferase gene expression was induced by treatment with PB201 in stably transfected HepG2 (human liver), AREc32 (human breast), MCF7 (human breast), A549 (human lung), 293T (human kidney), and A172 (human brain) cancer cell lines.
Figure 5:
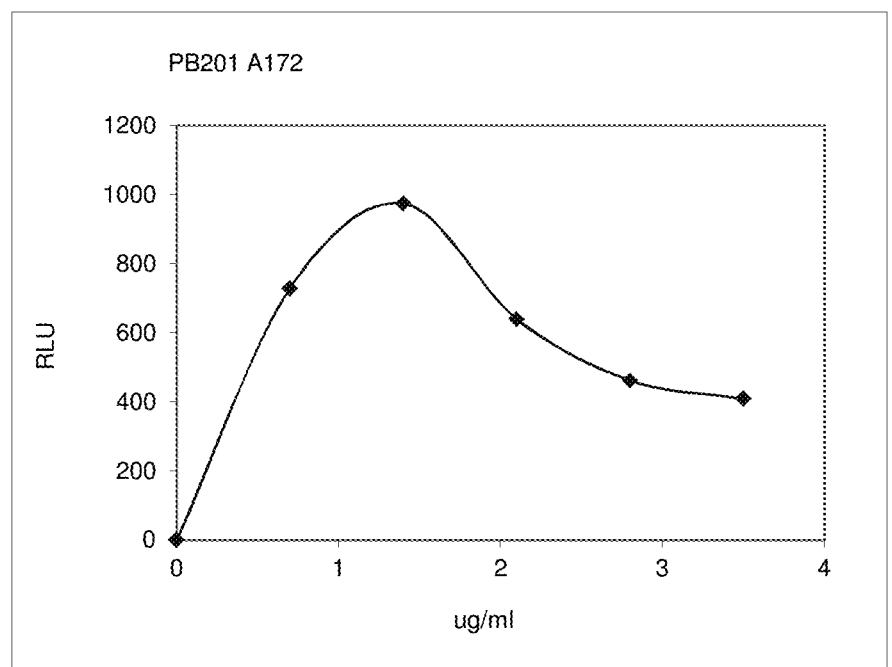
FIG. 5 shows relative light units (RLU) observed with added luciferin after ARE-driven luciferase gene expression was induced by treatment with PB201 in stably transfected A172 (human brain) cancer cell line.

Briefly, the stably transfected cells of types HepG2 (human liver), AREc32 (human breast), MCF7 (human breast), A549 (human lung), 293T (human kidney), and A172 (human brain) were seeded at low density in 24-well plates and incubated at 37° C. with 10% $CO_2$. After 24 h various concentrations of combinations of agents were added to the cells. After an additional 18 h of incubation, the cells were lysed in their wells with 100 µl of a lysing buffer that contains 3.5 mM sodium pyrophosphate to stabilize light output by luciferase. A 20 µl aliquot of cell lysate was added to a small test tube, placed in a BD Monolight 3010 luminometer for background luminescence, and then 50 µl of 1 mM luciferin was injected into the tube. Relative Light Units integrated for 10 sec were measured for each sample. The liver, breast, and kidney cell types tested exhibited Nrf2 gene activation and luciferase expression by treatment with PB201, with a lesser activation in the lung cells, and no activation in the brain cells in this experiment (FIGS. 2-4). Other experiments with the A172 human brain cell line revealed lower, but measurable, induction of Nrf2-dependent luciferase gene expression (FIG. 5). The A549 lung cancer cells already possess constitutive activation of Nrf2 due to a mutation, so were observed to have low or negative response to further stimulation with known Nrf2 activators or with PB201.

EXAMPLE 2

Cell Protective Mechanisms Induced by PB201 Treatment

As an example of the cell protective mechanisms induced by PB201 treatment, gene upregulation in cells treated with PB201 was examined. Briefly, cultured HepG2 liver cells were treated with PB201 at 1.5 micrograms/mL concentration for 18 hours, then total RNA was extracted from the HepG2 cells by using the RNeasy Total RNA Isolation Kit (QIAGEN Inc. Valencia, Calif., USA). The concentration of each sample was determined based on the absorbance at 260 nm (A260). The purity of each sample was determined based on the ratio of A260 to A280. A range of 1.9-2.1 was considered adequately pure. The integrity of Total RNA samples was verified by Agilent 2200 Tape Station. Total RNA (250ng) was converted to double-stranded cDNA (ds-cDNA) by using the cDNA synthesis kit (Affymetrix). An oligo-dT primer containing a T7 RNA polymerase promoter was utilized. The ds-cDNA was then purified and recovered by using purification beads (Affymetrix). Next, in vitro transcription was performed to generate biotin-labeled cRNA using a RNA Transcript Labeling Kit (Affymetrix). Biotin-labeled cRNA was purified using an RNeasy affinity column (Qiagen).

To ensure optimal hybridization to the oligonucleotide array, the cRNA was fragmented. Fragmentation was performed such that the cRNA fragments are between 50-200 bases in length by incubating the cRNA at 94° C. for 35 min in a fragmentation buffer. The sample was then added to a hybridization solution containing 100 mM MES, 1 M Na+, and 20 mM EDTA in the presence of 0.01% Tween 20. The final concentration of the fragmented cRNA was 0.05 µg/µL. Hybridization was performed by incubating 200 uL of the sample to the Affymetrix GeneChip® PrimeView™ human gene expression array (Affymetrix Inc., Santa Clara, Calif., USA) at 45° C. for 16 hours using a GeneChip® Hybridization Oven 640 (Affymetrix).

After hybridization, the hybridization solutions were removed and the arrays were washed and stained with Streptavidin-phycoerythrin using a GeneChip® Fluidics Station 450 (Affymetrix). Arrays were read at a resolution of 2.5 to 3 microns using the GeneChip Scanner 3000 (Affymetrix). Each gene was represented by the use of ~11 probes per transcript and many control probes. The Command Console GeneChip software program was used to determine the intensity of expression for all genes on the array. For this experiment, fold-induction of genes by PB201 treatment of HepG2 cells was calculated compared to the average intensity observed in control HepG2 cells in culture solution without any added stimulus such as PB201.

As depicted in Table 1, the top 28 genes upregulated by PB201 included a variety of antioxidant, anti-inflammatory, and cell stress protective genes, of which 14 of the top 28 are known to be regulated by the Nrf2 transcription factor (GSTA1, AKR1C2, AKR1B10, AKR1C1, PTGR1, CYP4F11, GCLM, HMOX1, OSGIN1, AQP3, SQSTM1, SRXN1, FTH1, and AGPAT9). This example supports that the mechanism of cellular protection by PB201 involves activation of the Nrf2 cell signaling pathway.

TABLE 1

Top 28 genes upregulated by PB201 in HepG2 cells

| HepG2 centrol signal | Fold induction by 9B201 | Gene Title | Gene Symbol | Known to be regulated by Nrf2? |
|---|---|---|---|---|
| 59.22 | 6.99 | glutathione S-transferase alpha 1 /// glutathione S-transferase alpha 2 | GSTA1 /// GSTA2 | yes |
| 2435.26 | 6.56 | aldo-keto reductase family 1, member C2 (dihydrodiol dehydrogenase 2; bile acid binding protein; 3-alpha hydroxysteroid dehydrogenase, type III) /// aldo-keto reductase family 1 member C2-like | AKR1C2 /// LOC100653286 | yes |
| 1112.08 | 5.85 | aldo-keto reductase family 1, member B10 (aldose reductase) /// aldo-ketc reductase family 1, member B15 | AKR1B10 /// AKR1B15 | yes |
| 2722.97 | 4.97 | aldo-keto reductase family 1, member C1 (dihydrodiol dehydrogenase 1; 20-alpha (3-alpha)-hydroxysteroid dehydrogenase) | AKR1C1 | yes |
| 499.98 | 4.79 | prostaglandin reductase 1 | PTGR1 | yes |
| 63.77 | 4.43 | cytochrome P450, family 4, subfamily F, polypeptide 11 | CYP4F11 | yes |
| 19.53 | 4.18 | EP300 interacting inhibitor of differentiation 3 | EID3 | |
| 570.86 | 4.10 | aldo-keto reductase family 1, member B15 | AKR1B15 | |
| 117.73 | 4.03 | glutamate-cysteine ligase, modifier subunit | GCLM | yes |
| 21.04 | 3.90 | kynureninase | KYNU | |
| 180.89 | 3.80 | betaine-homocysteine S-methyltransferase 2 | BHMT2 | |
| 43.64 | 3.80 | solute carrier family 16, member 6 (monocarboxylic acid transporter 7) | SLC16A6 | |
| 331.00 | 3.64 | heme oxygenase (decycling) 1 | HMOX1 | yes |
| 63.38 | 3.51 | transient receptor potential cation channel, subfamily V, member 3 | TRPV3 | |
| 231.82 | 3.18 | oxidative stress induced growth inhibitor 1 | OSGIN1 | yes |
| 113.36 | 3.00 | testis expressed 19 | TEX19 | |
| 86.47 | 3.00 | aquaporin 3 (Gill blood group) | AQP3 | yes |
| 44.71 | 2.91 | FBJ murine osteosarcoma viral oncogene homolog | FOS | |
| 69.00 | 2.88 | pannexin 2 | PANX2 | |
| 554.60 | 2.84 | sequestosome 1 | SQSTM1 | yes |
| 1908.04 | 2.80 | sulfiredoxin 1 | SRXN1 | yes |
| 50.59 | 2.71 | myeloid/lymphoid or mixed-lineage leukemia (trithorax homolog, *Drosophila*); translocated to, 11 | MLLT11 | |
| 771.67 | 2.62 | ferritin, heavy polypeptide 1 | FTH1 | yes |
| 214.48 | 2.59 | galactosidase, alpha | GLA | |
| 257.63 | 2.55 | tubulin, alpha 4a | TUBA4A | |
| 73.86 | 2.51 | cell cycle progression 1 /// DYX1C1-CCPG1 readthrough (non-protein coding) | CCPG1 /// DYX1C1-CCPG1 | |
| 69.77 | 2.46 | cytochrome P450, family 4, subfamily F, polypeptide 3 | CYP4F3 | |
| 488.83 | 2.46 | 1-acylglycerol-3-phosphate O-acyltransferase 9 | AGPAT9 | yes |

EXAMPLE 3

Improving Aqueous Distribution of 1,3-diphenyl-1,3-propanedione

Figure 6:
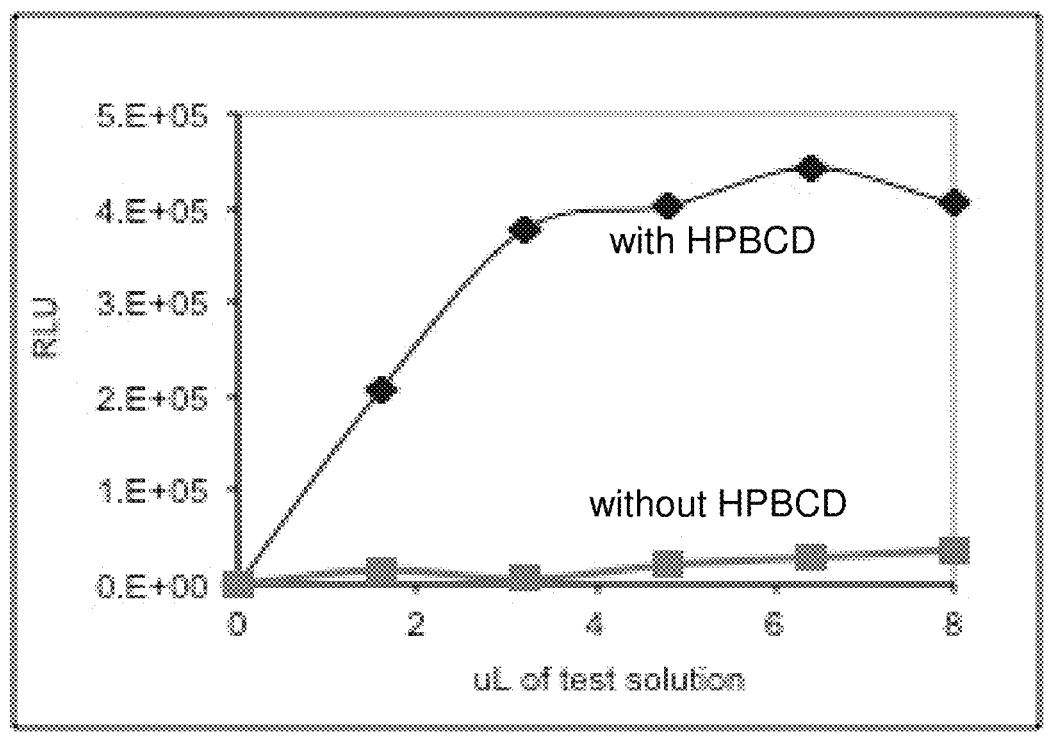
FIG. 6 shows increased the solubility of PB201 in aqueous solution.

In this example, approaches were used to increase the aqueous distribution of the otherwise relatively insoluble 1,3-diphenyl-1,3-propanedione (DBM) by adding 2-hydroxypropyl beta-cyclodextrin (HPBCD) at a molar ratio (DBM:HPBCD) of 1:3. 1,3-diphenyl-1,3-propanedione exhibits low aqueous solubility alone due to its lipophilic properties, but the addition of 2-hydroxypropyl beta-cyclodextrin allows the HPBCD molecules to interact with the phenyl group moieties on each end of the 1,3-diphenyl-1,3-propanedione molecule, masking their lipophilic properties and improving the aqueous characteristics of 1,3-diphenyl-1,3-propanedione by masking the lipophilic phenyl groups with the hydrophilic exterior of the 2-hydroxypropyl beta-cyclodextrin molecules and improving the aqueous characteristics of 1,3-diphenyl-1,3-propanedione (FIG. 6). PB201 is nearly insoluble in water or aqueous solutions alone, so 5 mg samples of PB201 were prepared in 1 mL aqueous phosphate buffered saline, with and without 93 mg (3:1 mole ratio) of 2-hydroxypropyl beta-cyclodextrin (HPBCD) added. The PB201 visually dissolved in the HPBCD/PBS but not the PBS. To verify its presence in the aqueous solutions, the samples were tested for activity of PB201 using HepG2-ARE promoter/reporter cells, which are responsive to PB201 and other Nrf2-activators by promoting the expression of luciferase. In this case Nrf2 was activated by the PB201 in HPBCD/PBS but not by PB201 in PBS alone, measured as chemiluminescent signal (RLU), indicating that 2-hydroxypropyl beta-cyclodextrin greatly increased the solubility of PB201 in aqueous solution, and supporting its use in creating aqueous PB201 formulations for administration to the oral mucosa.

Furthermore, the Nrf2 activation by the 1,3-diphenyl-1,3-propanedione, with or without solubility enhancing agents such as HPBCD, is temporary, not permanent, and can be repeated; for example the Nrf2 activation by 4.2 ug/mL 1,3-diphenyl-1,3-propanedione decreases from its level at 17 hours (72,949 RLU) to 24 hours (47,121 RLU) after stimulation, and is nearly back to its baseline, unstimulated levels (7182 RLU) by 48 hours (11,659 RLU). Similarly, other types of agents can be utilized to increase aqueous levels of 1,3-diphenyl-1,3-propanedione including, but not limited to, surfactants, liposomes, amphiphiles, emulsifiers, and complexing agents to make solutions or suspensions.

EXAMPLE 4

Time Course of PB201 on the Nrf2 Signaling Pathway

Figure 7:
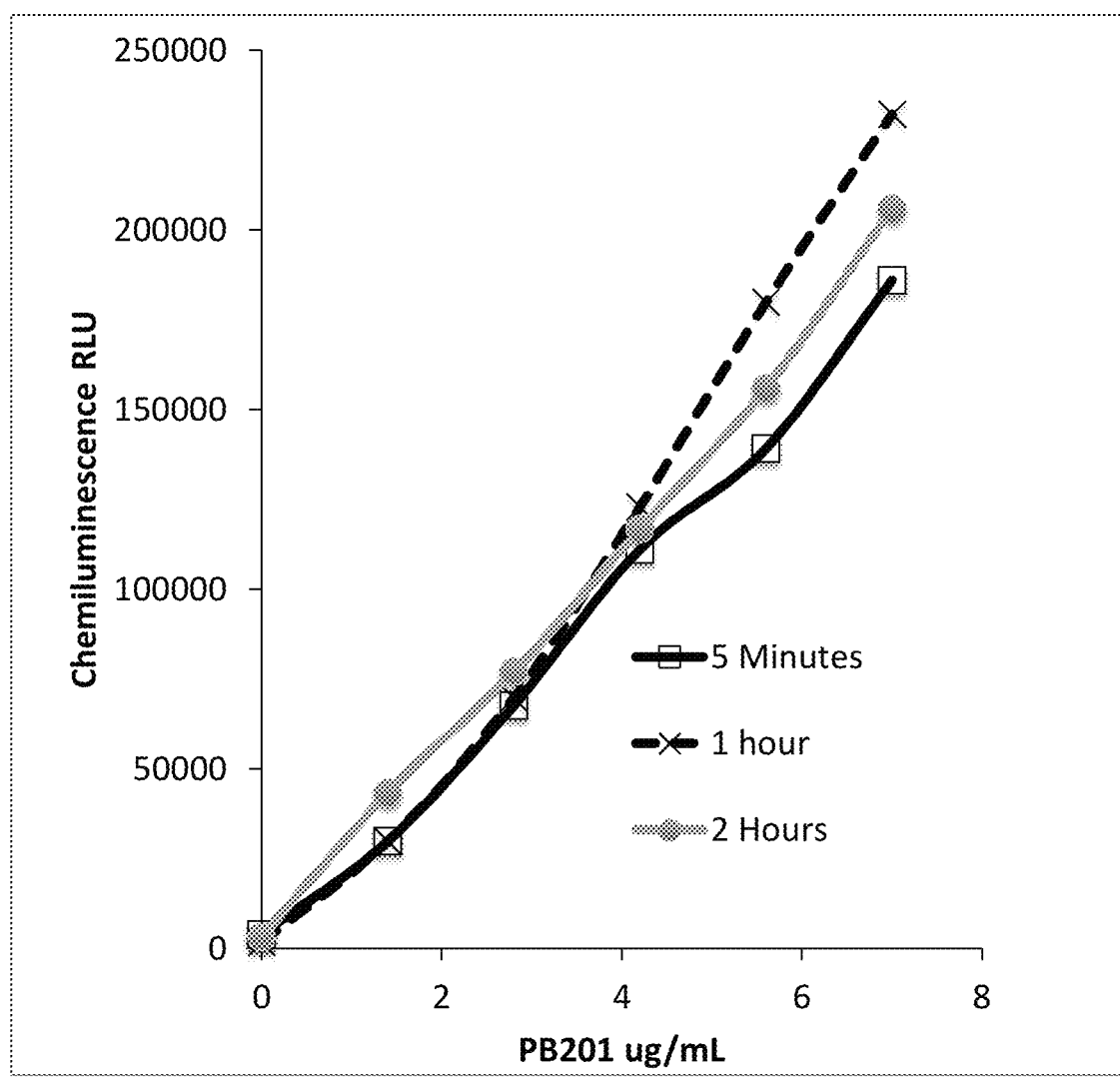
FIG. 7 shows Nrf2 Induction in HepG2-ARE cells treated with PB201 at 0-7 ug/mL for 5 min, 1 h, or 2 h, and then chemiluminescence response read 24 h after start of stimulation.

As an example of the short time course of PB201 exposure needed to activate the Nrf2 signaling pathway, HepG2 cells stably transfected with a Nrf2-driven promoter, luciferase reporter construct were treated with PB201 for 5 minutes, 1 hour, or 2 hours, then the PB201 was removed and washed off the cells, then 24 hours later the luciferase levels were measured by chemiluminescence to assay for Nrf2 activation. Even the short time exposure of 5 minutes led to a strong Nrf2 response similar to 1 or 2 hours of exposure, indicating that temporary topical application could still create a strong upregulation of Nrf2-dependent genes (FIG. 7)

EXAMPLE 5

1,3-diphenyl-1,3-propanedione Derivatives or Analogs

Figure 8:
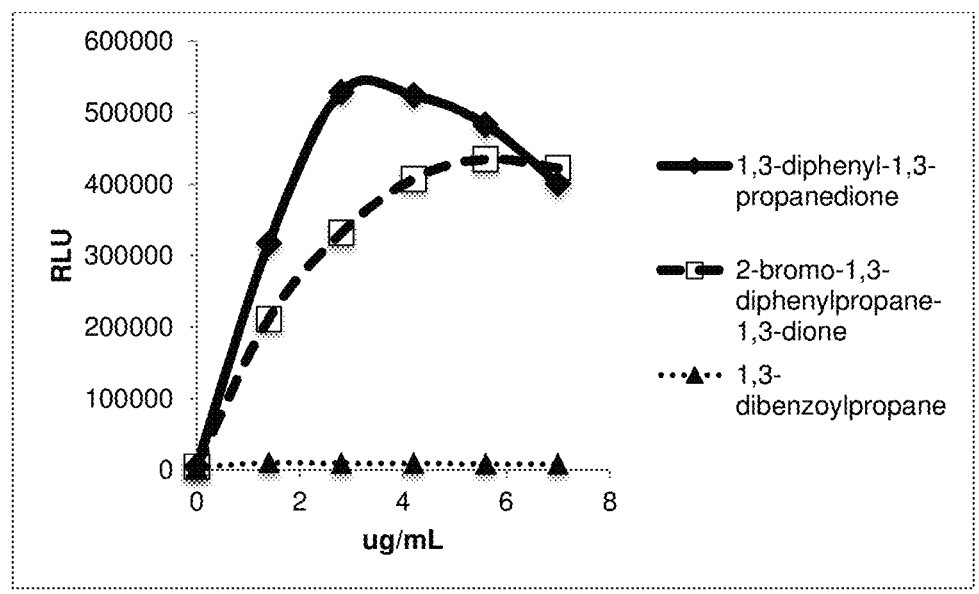
FIG. 8 shows Nrf2 Induction in HepG2-ARE cells treated with PB201 analogs at 0-7 ug/mL with chemiluminescence response read 24 h after start of stimulation.

In this Example, the effects of compounds that are structurally related to 1,3-diphenyl-1,3-propanedione are investigated. A halogenated analog (2-bromo-1,3-diphenyl-1,3-propanedione and an analog with a longer hydrocarbon chain between the phenyl groups (1,3-dibenzoylpropane) activated Nrf2 in HepG2 cells stably transfected with a Nrf2/ARE promoter-luciferase reporter construct (FIG. 8).

EXAMPLE 6

Cell Protective Mechanisms Induced by PB201 Treatment

Figure 9:
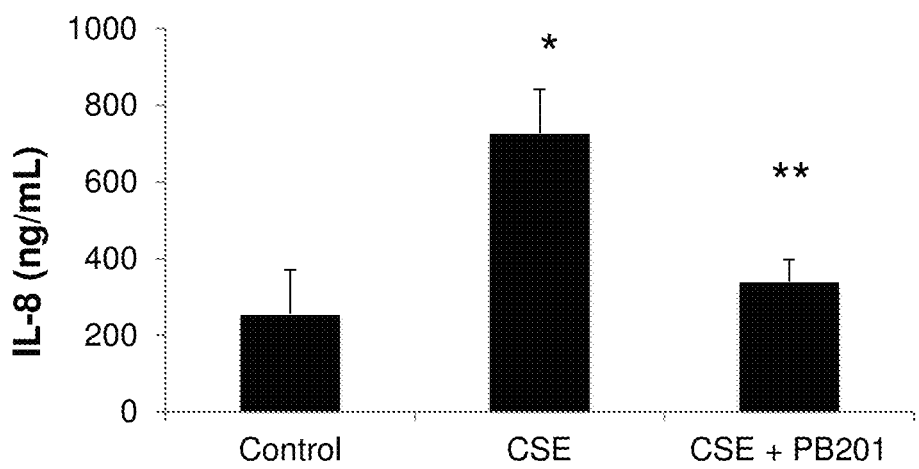
FIG. 9 shows PB201 significantly decreased IL-8 release from primary human lung epithelial cells exposed to CSE for 7 days (*p<0.05 compared to control, "p<0.05 compared to CSE).

As an example of the cell protective mechanisms induced by PB201 treatment, release of the proinflammatory cytokine Interleukin-8 (IL-8) was attenuated in primary human lung epithelial cells treated with PB201 compared to untreated cells when both were stimulated with cigarette smoke extract (FIG. 9).

EXAMPLE 7

Effects of PB201 on Oral Mucositis

A formulation of PB201 was administered topically within the oral cavity daily to a mammal receiving radiation treatment or chemotherapy that can cause oral mucositis as a side effect. PB201 administration decreased the frequency and/or severity of the oral mucositis as compared to untreated or placebo treated subjects.

Administration of PB201 formulations onto the cheek pouch surface of Syrian Golden Hamsters protected against the oral mucositis that otherwise occurred following a single dose of radiation to the cheek pouch. In this example, a single dose of radiation (40 Gy) was given on day 0 to the isolated cheek pouch and PB201 treatment was given by topical cheek pouch administration of 1 to 10 µg PB201 given three times daily from days 0 to 28 as 0.2 mL of 5 µg/mL given 3×/day or 0.2 mL of 50 µg/mL given 3×/day, and oral mucositis was determined as cheek pouch ulceration, scored every 2 days from days 6 to 28. Mucositis was scored visually by comparison to a validated photographic scale, ranging from 0 (normal) to 5 (severe ulceration). In descriptive terms, this scale is defined as follows.

TABLE 2

| Score: | Description: |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/grey due to pseudomembrane. Cumulative size of ulcers should equal about ¼ of the pouch. Severe erythema and vasodilation. |
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth) |

A score of 1-2 is considered to represent a mild stage of the disease, whereas a score of 3-5 is considered to indicate moderate to severe mucositis. By this example, PB201 has been shown to have protective effects against radiation-induced oral mucositis The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of microbiology, molecular biology and cell biology, which are well known in the art.

The disclosed methods and systems may be modified without departing from the scope hereof. It should be noted that the matter contained in the above description or shown in the accompanying drawings should be interpreted as illustrative and not in a limiting sense.

LIST OF REFERENCES

The following references, patents and publication of patent applications are either cited in this disclosure or are of relevance to the present disclosure. All documents listed below, along with other papers, patents and publication of patent applications cited throughout this disclosures, are hereby incorporated by reference as if the full contents are reproduced herein.

Cho, H. Y. and S. R. Kleeberger (2010). "Nrf2 protects against airway disorders." Toxicol Appl Pharmacol 244 (1): 43-56.

Eggler, A. L., K. A. Gay and A. D. Mesecar (2008). "Molecular mechanisms of natural products in chemoprevention: induction of cytoprotective enzymes by Nrf2." Mol Nutr Food Res 52 Suppl 1: S84-94.

Elad, S., I. Meidan, G. Sellam, S. Simaan, I. Zeevi, E. Waldman, M. Weintraub and S. Revel-Vilk (2013). "Topical curcumin for the prevention of oral mucositis in pediatric patients: case series." Altern Ther Health Med 19(3): 21-24.

Francis, M. and S. Williams (2014). "Effectiveness of Indian Turmeric Powder with Honey as Complementary Therapy on Oral Mucositis: A Nursing Perspective among Cancer Patients in Mysore." Nurs J India 105(6): 258-260.

Gao, B., A. Doan and B. M. Hybertson (2014). "The clinical potential of influencing Nrf2 signaling in degenerative and immunological disorders." Clin Pharmacol 6: 19-34.

Huang, Y., W. Li, Z.-y. Su and A.-N. T. Kong (2015). "The complexity of the Nrf2 pathway: Beyond the antioxidant response." The Journal of Nutritional Biochemistry: in press.

Koehn, F. E. and G. T. Carter (2005). "The evolving role of natural products in drug discovery." Nat Rev Drug Discov 4(3): 206-220.

Lee, K. H. (2010). "Discovery and development of natural product-derived chemotherapeutic agents based on a medicinal chemistry approach." J Nat Prod 73(3): 500-516.

Luer, S., R. Troller, M. Jetter, V. Spaniol and C. Aebi (2011). "Topical curcumin can inhibit deleterious effects of upper respiratory tract bacteria on human oropharyngeal cells in vitro: potential role for patients with cancer therapy induced mucositis?" Support Care Cancer 19(6): 799-806.

Luer, S. C., J. Goette, R. Troller and C. Aebi (2014). "Synthetic versus natural curcumin: bioequivalence in an in vitro oral mucositis model." BMC Complement Altern Med 14: 53.

Maher, J. and M. Yamamoto (2010). "The rise of antioxidant signaling—the evolution and hormetic actions of Nrf2." Toxicol Appl Pharmacol 244(1): 4-15.

Niture, S. K., R. Khatri and A. K. Jaiswal (2014). "Regulation of Nrf2—an update." Free Radical Biology and Medicine 66: 36-44.

Reisman, S. A., A. R. Goldsberry, C. Y. Lee, M. L. O'Grady, J. W. Proksch, K. W. Ward and C. J. Meyer (2015). "Topical application of RTA 408 lotion activates Nrf2 in human skin and is well-tolerated by healthy human volunteers." BMC Dermatol 15(1): 10.

Reisman, S. A., C. Y. Lee, C. J. Meyer, J. W. Proksch, S. T. Sonis and K. W. Ward (2014). "Topical application of the synthetic triterpenoid RTA 408 protects mice from radiation-induced dermatitis." Radiat Res 181(5): 512-520.

Reisman, S. A., C. Y. Lee, C. J. Meyer, J. W. Proksch and K. W. Ward (2014). "Topical application of the synthetic triterpenoid RTA 408 activates Nrf2 and induces cytoprotective genes in rat skin." Arch Dermatol Res 306(5): 447-454.

Rezvani, M. and G. A. Ross (2004). "Modification of radiation-induced acute oral mucositis in the rat." Int J Radiat Biol 80(2): 177-182.

Satoh, H., T. Moriguchi, K. Taguchi, J. Takai, J. M. Maher, T. Suzuki, P. T. Winnard, Jr., V. Raman, M. Ebina, T. Nukiwa and M. Yamamoto (2010). "Nrf2-deficiency creates a responsive microenvironment for metastasis to the lung." Carcinogenesis 31(10): 1833-1843.

Shukla, S. J., R. Huang, S. O. Simmons, R. R. Tice, K. L. Witt, D. Vanleer, R. Ramabhadran, C. P. Austin and M. Xia (2012). "Profiling environmental chemicals for activity in the antioxidant response element signaling pathway using a high throughput screening approach." Environ Health Perspect 120(8): 1150-1156.

Simmons, S. O., C. Y. Fan, K. Yeoman, J. Wakefield and R. Ramabhadran (2011). "NRF2 Oxidative Stress Induced by Heavy Metals is Cell Type Dependent." Curr Chem Genomics 5: 1-12.

Sonis, S. T. (2011). "Oral mucositis." Anticancer Drugs 22(7): 607-612.

Villa, A. and S. T. Sonis (2015). "Mucositis: pathobiology and management." Curr Opin Oncol 27(3): 159-164.

Yuan, A. and S. Sonis (2014). "Emerging therapies for the prevention and treatment of oral mucositis." Expert Opin Emerg Drugs 19(3): 343-351.

What is claimed is:

1. A method for prevention or treatment of oral mucositis in a mammal, comprising administering to the mammal a composition comprising a therapeutically effective amount of 1,3-diphenyl-1,3-propanedione (DBM), wherein formulation of DBM further comprises aloe extract as a viscous liquid or gel carrier, and wherein the formulation of DBM is in a form selected from the group consisting of liquid solutions, suspensions, gels, lotions, ointments mouthwashes, sprays, and combination thereof.

2. A method for prevention or treatment of oral mucositis in a mammal, comprising administering to the mammal a composition comprising a therapeutically effective amount of 1,3-diphenyl-1,3-propanedione (DBM), wherein the composition is applied topically at least once daily and the dosage of DBM is between 10 μg and 1000 μg.

3. The method of claim 2, wherein the DBM is an aqueous solution with concentration of DBM being between 5 and 50 μg/mL (22 to 223 μM), wherein volume of said composition is sufficient to cover said oral mucositis.

4. The method of claim 1, wherein the mammal is a human.

5. The method of claim 1, wherein the administration is by applying the composition to oral cavity of a mammal.

6. The method of claim 1, wherein the mammal has a disease or condition selected from the group consisting of oxidative stress, detoxification, inflammation, and cancer prior to said administration.

7. The method of claim 1, wherein the mammal has a disease or condition caused by a treatment selected from the group consisting of radiation therapy and chemotherapy prior to said administration.

8. The method of claim 1, wherein the mammal has a radiation-induced oral mucositis or chemotherapy-induced oral mucositis prior to said administration.

9. A method for prevention or treatment of oral mucositis in a mammal, comprising administering to the mammal a composition comprising a therapeutically effective amount of 1,3-diphenyl-1,3-propanedione (DBM), wherein the composition further comprises a solubility enhancing agent 2-hydroxypropyl beta-cyclodextrin (HPBCD).

10. The method of claim 9, wherein the molar ratio between DBM and HPBCD is between about 1:1 and 1:5.

11. The method of claim 9, wherein the composition is applied topically at least once daily, said composition comprising an aqueous DBM solution with concentration of DBM being between 5 and 50 μg/mL (22 to 223 μM), wherein volume of said composition is sufficient to cover the oral mucositis surface.

12. The method of claim 9, wherein the composition is applied topically at least once daily and the dosage of DBM is between 10 μg and 1000 μg.

13. The method of claim 2, wherein the mammal is a human.

14. The method of claim 2, wherein the administration is by applying the composition to oral cavity of a mammal.

15. The method of claim 2, wherein the mammal has a radiation-induced oral mucositis or chemotherapy-induced oral mucositis prior to said administration.

16. The method of claim 9, wherein the mammal is a human.

17. The method of claim 9, wherein the administration is by applying the composition to oral cavity of a mammal.

18. The method of claim 9, wherein the mammal has a radiation-induced oral mucositis or chemotherapy-induced oral mucositis prior to said administration.

* * * * *